United States Patent [19]

Felix

[11] Patent Number: 5,011,990

[45] Date of Patent: Apr. 30, 1991

[54] PROCESS FOR THE PREPARATION OF N-ALLYLAMIDES FROM O-ALLYLIMIDATES

[76] Inventor: Raymond A. Felix, 5949 Ralston Ave., Richmond, Calif. 94805

[21] Appl. No.: 291,082

[22] Filed: Dec. 27, 1988

[51] Int. Cl.$^5$ .................................... C07C 233/13
[52] U.S. Cl. .................... 564/161; 564/204; 585/377; 585/531; 585/620
[58] Field of Search ............... 260/404; 564/161, 204, 564/208; 502/200; 585/377, 531, 670; 71/86

[56] References Cited

PUBLICATIONS

Schenck et al., JACS, 1985, 107: 2058–2066.
Ikariya et al., Chemistry Letters, 1982, pp. 1815–1818.
Overman, Angew. Chem. Int. Ed. Engl., 1984, 23: 579–586.
Tamaru et al., J. Org. Chem., 1980, 45: 5221–5223.
Tamaru et al., J. Org. Chem., 1983, 48: 1293–1297.

Primary Examiner—Glennon H. Hollrah
Assistant Examiner—Brian Bembenick

[57] ABSTRACT

Compounds having the formula

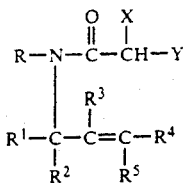

wherein R is an aromatic or aliphatic group; $R^1$, $R^2$, $R^3$, $R^4$ and $R^5$ are independently hydrogen, $C_{1-4}$ alkyl or phenyl; X is halogen; and Y is halogen or an aromatic group; are prepared in a regioselective manner by treating a compound having the formula

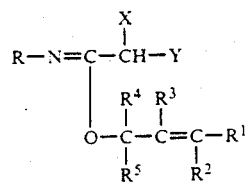

with a catalytic amount of a palladium(O) or a palladium(II) transition metal catalyst.

14 Claims, No Drawings

PROCESS FOR THE PREPARATION OF N-ALLYLAMIDES FROM O-ALLYLIMIDATES

BACKGROUND OF THE INVENTION

The present invention is related to an improved process for the manufacture of halogen-substituted N-allylamides from halogen-substituted O-allylimidates using palladium transition metal catalysts.

N-allylamides are useful as pesticides and as intermediates in the preparation of pesticides. A method for synthesizing these amides is by a Claisen rearrangement of O-allylimidates. Unfortunately, the Claisen method requires very high temperatures, typically of 200° C. and above. Also, when a halogen-substituted methyl group is present on the 2-carbon of the imidate, use of the method results in a mixture of compounds but no desired product. The high temperature required for the rearrangement appears to destroy the starting material.

A procedure has been reported which uses transition metals, including zero-valent palladium (Pd(O)) or two-valent palladium (Pd(II)), as catalysts in Claisen rearrangements.

Schenck et al. (JACS, 1985, 107: 2058-2066) discuss the use of Pd(O) and Pd(II) catalysts, in addition to other transition metals, on a variety of allylimidate compounds, none of which imidates include a halogen-substituted methyl at the 2-position. The data in the article indicate that there are major differences between the Pd(O) and Pd(II). The reaction runs much more slowly with the Pd(II) than with the Pd(O). Also, reaction with Pd(II) always gives products with the desired regioselectivity (i.e., a [3.3]-sigmatropic shift) whereas reaction with Pd(O) produces either a mixture of Claisen ([3.3]-sigmatropic) and anti-Claisen ([1.3]sigmatropic) products or all anti-Claisen product, apparently due to the presence of a $\pi$-allyl intermediate. The data also indicate that the presence of a substituent on the 2-carbon has a marked effect on the velocity of the reaction; it slows the reaction down considerably.

Ikariya et al. (Chemistry Letters, 1982, pp. 1815-1818) discuss the use of Pd(O) and Pd(II) as catalysts in the rearrangement of O-allyl-N-phenylformimidates to give N-allyl-N-phenylformamides. The only substituents shown on the 2-carbon are hydrogen and phenyl. Halogen-substituted methyl groups at that position are not disclosed. Ikariya et al. agree with Schenck et al. that the catalytic activity of Pd(O) is much higher than that of Pd(II) and that Pd(II) is regioselective while Pd(O) is not. In contrast to Schenck et al., Ikariya et al. note an apparent slight acceleration of the rearrangement when a substituent, here phenyl, is present on the 2-carbon of the imidate.

Overman (Angew. Chem. Int. Ed. Engl., 1984, 23: 579-586) discusses generally allylic ester rearrangements using Hg(II) and Pd(II) salts as catalysts. Rearrangement of imidates is not discussed in the article. Tamaru et al. (J. Org. Chem., 1980, 45: 5221-5223) address only palladium-catalyzed rearrangement of S-allylthioimidates to give N-allylthioamides and observe that while Pd(II) gave the desired product, Pd(O) did not. The thiono-thiolo allylic rearrangement of O-allyl phosphoro- and phosphonothionates by catalysis with Pd(O) is described by Tamaru et al. in J. Org. Chem., 1983, 48: 1293-1297. This reaction gave mainly products in which the sulfur atom was bonded to the least substituted carbon atom, regardless of the substitution pattern of the allylic groups. Thus, for example, O-crotyl was converted to S-crotyl rather than to S-(1-methyl)allyl. Contrary to other reports, in this case Pd(II) was generally not effective.

SUMMARY OF THE INVENTION

It has now been discovered that when a halogen-substituted methyl is present on the 2-carbon of O-allylimidates, treatment of the imidate in the presence of either a Pd(O) or a Pd(II) metal transition catalyst will result in rearrangement to N-allylamides in high yields, under mild conditions and with all product of the desired [3.3]-sigmatropic regioselectivity, regardless of which of the catalysts is used.

DETAILED DESCRIPTION OF THE INVENTION

More particularly, this invention is directed to a process for the manufacture of a compound having the formula

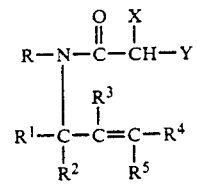

wherein,

R is an unsubstituted or substituted aromatic group or an unsubstituted or substituted aliphatic group;

each of $R^1$, $R^2$, $R^4$ and $R^5$ is independently selected from hydrogen, $C_{1-4}$ alkyl or phenyl;

X is halogen; and

Y is halogen or an unsubstituted or substituted aromatic group;

which process comprises the rearrangement of a compound having the formula

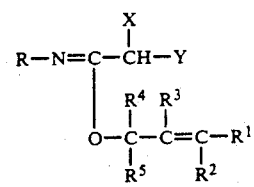

wherein R, $R^1$, $R^2$, $R^3$, $R^4$, $R^5$, X and Y are as defined above, by treatment of the compound II with a catalytic amount of a palladium(O) or a palladium(II) transition metal catalyst.

The term "aromatic group" refers to a hydrocarbon group having from five to twenty carbon atoms and containing at least one unsaturated carbon ring. Examples of aromatic groups include phenyl and naphthyl.

The term "aliphatic group" refers to both cyclic and open-chain carbon groups, either branched or straight, having from one to twenty carbon atoms, such as the alkyls, the alkenyls, the alkynyls, the cycloalkyls and the cycloalkenyls.

The term "substituted aromatic" refers to an aromatic group substituted at one to five of the carbon atoms with groups such as halogen, cyano, nitro, $C_{1-6}$ alkyl, $C_{1-6}$ haloalkyl, $C_{1-6}$ alkoxy or $C_{1-6}$ haloalkoxy.

The term "substituted aliphatic" refers to an aliphatic group substituted at one to eight of the carbon atoms with groups such as halogen, cyano, nitro, the aromatics. $C_{1-6}$ alkyl, $C_{1-6}$ haloalkyl, $C_{1-6}$ alkoxy or $C_{1-6}$ haloalkoxy.

Where any of the substituents R. X and Y is or comprises halogen, such halogen is conveniently selected from bromo, chloro or fluoro.

Within the scope of the above description, certain embodiments are preferred:

In the description of R. unsubstituted or substituted aromatics are preferred; phenyl substituted at one to five of the ring carbon atoms with halogen. trifluoromethyl, cyano, $C_{1-4}$ alkyl or $C_{1-4}$ alkoxy is more preferred.

In each of $R^1$-$R^5$, hydrogen, methyl or ethyl are preferred.

In X, chloro is preferred.

In Y, chloro or phenyl (substituted at one to five of the ring carbon atoms with hydrogen, halogen, trifluoromethyl, cyano, $C_{1-4}$ alkyl or $C_{1-4}$ alkoxy) are preferred.

Any zero-valent or two-valent palladium transition metal catalyst may be used in the present invention. The term "palladium (O) or palladium (II) transition metal catalyst" is used herein to designate a catalyst consisting of Pd(O) or Pd(II) metal chemically bound with other elements in the form of metal-containing compounds, such as salts and oxides. The metal-containing compounds can also be present in the form of complexes with common complexing agents, examples of which are triphenylphosphine, carbon monoxide and tertiary amines. A preferred Pd(O) transition metal catalyst is tetrakis(triphenylphosphine)palladium (Pd(PPh$_3$)$_4$) Preferred Pd(II) transition metal catalysts include palladium acetate (Pd(OAc)$_2$), palladium acetylacetonate, palladium chloride, or palladium chloride complexes of acetonitrile (PdCl$_2$(MeCN)$_2$) or of benzonitrile (PdCl$_2$(PhCN)$_2$) Such catalysts may be used singly or in mixtures.

The Pd(O) or Pd(II) transition metal catalyst is present in the reaction in a catalytic amount. The quantity which will constitute a "catalytic amount" will be any quantity that serves to increase the rate of reaction, with larger quantities providing a greater increase. The quantity used in any particular application will be determined in large part by the individual needs of the manufacturing facility. Factors which enter into such a determination include the catalyst cost, recovery costs, desired reaction time, and system capacity. Aside from these considerations, the catalyst quantity is not a critical feature of the invention and can vary over a wide range. It will be most convenient to use an amount of catalyst which comprises from about 0.01 to about 20.0 mole percent, preferably from about 0.1 to about 10.0 mole percent.

While the thermal Claisen rearrangement of allyl imidates typically requires reaction for several hours at ca. 200° C. or above for completion (Schenck et al., supra). the process of the present invention allows reaction under milder conditions and with shorter reaction times. Thus, the reaction may take place at a temperature of from about 20° C. to about 160° C., with about 80 C. to about 150° C. preferred. The reaction typically is complete in 1 to 2 hours or less.

The reaction may or may not be conducted under an inert gas atmosphere, depending on the amount of metal catalyst used and rate of the reaction. Where a larger amount of metal is present and/or where the reaction takes place over a longer period of time, so that there is a greater possibility that the metal would oxidize to a higher oxidation state when exposed to oxygen, the reaction should be run under an inert gas atmosphere. Any inert gas may be used in the practice of this invention. Examples include argon, helium, neon and nitrogen, although nitrogen is preferred due to availability and lower cost.

The process does not have a critical operating pressure, but is operable over a wide pressure range, subject only to considerations of economy and materials of construction. It is most convenient, however, to conduct the reaction at approximately atmospheric pressure.

Although the reaction can be conducted without the use of a solvent, a variety of solvents can be used to facilitate the handling of the system components, to aid in solubilization of the catalyst if desired, to facilitate agitation, and to improve reaction control by minimizing decompositions and by-product formation and by controlling reaction rate. Any inert solvent can be used, including, but not limited to the following: aliphatic compounds, for example heptane or octane; aromatic compounds, for example benzene, toluene, xylene or mesitylene; chlorinated aliphatic or aromatic compounds, for example methylene chloride 1,2-dichloroethane or chlorobenzene; ethers, for example 1,2-dimethoxyethane, diethyl ether, tetrahydrofuran (THF) or 1,4-dioxane; alcohols, for example isopropanol or ethylene glycol; carboxylic acids, for example acetic, propionic or butyric acid; amides, for example N,N-dimethylformamide or N-methylpyrrolidinone; and nitriles, for example acetonitrile or butyronitrile. The reaction may be, and preferably is run without solvent.

The N-allylamides produced by the reaction of the invention can be recovered from the reaction mixture by any conventional technique. Examples of such techniques are solvent extraction, crystallization, sublimation and distillation.

The process of the invention gives only one product rather &than a mixture of products. The resulting product is of the desired [3.3] regioselectivity, whether Pd(O) or Pd(II) is used as the catalyst. Thus, for example, O-crotyl will be converted to N-(1-methyl)allyl and O-(1-methyl)allyl will be converted to N-crotyl. The presence of a halogen atom as a substituent off the 2-position of the imidate appears to avoid the π-allyl intermediate which destroys regioselectivity.

A halogen atom off the 2-position of the imidate also seems to overcome the adverse effect (enhanced π-allyl formation with resulting destruction of regioselectivity) of the presence of an electron-withdrawing group on the nitrogen. As a result, the substituent R may be either an electron-withdrawing or an electron-donating group.

The process of the present invention is further illustrated by the following examples. These examples are offered strictly for purposes of illustration, and are not intended to either limit or to define the invention. In each of the following examples, the yield indicated is the total yield of the reaction and is all of the desired [3.3] regioselectivity.

EXAMPLE 1

This example illustrates the preparation of N-allyl-N-(3-trifluoromethylphenyl)-(4-chloro)phenyl-chloroacetamide using a Pd(O) catalyst.

In a 100-mL flask under N2 atmosphere was placed O-allyl N-(3-trifluoromethylphenyl)-(4-chloro)phenyl-chloroacetamidate (10.4 g. 27.0 mmol) and tetrakis(triphenylphosphine)palladium(O) (Pd(PPh3)4 0.45 g. 0.4 mmol). The flask was equipped with magnetic stirring and was lowered into an oil bath at 120° C.±5° C. for 2 hours. The reaction mixture was cooled, diluted with ethyl ether and passed through an alumina pad to remove the metal catalyst. The ether was evaporated off to yield 7.9 g (76%) of N-allyl N-(3-trifluoromethylphenyl)-(4-chloro)phenylchloroacetamide, the structure of which was confirmed by nuclear magnetic resonance (NMR), infrared spectroscopy (IR) and mass spectroscopy (MS).

EXAMPLE 2

This example illustrates the preparation of N-allyl-(3-trifluoromethylphenyl)dichloroacetamide using a Pd(II) catalyst.

In a 100-mL flask under $N_2$ was placed O-allyl N-(3-trifluoromethylphenyl)dichloroacetamidate (5.0 g. 16.0 mmol) and palladium acetate (Pd(OAc)2; 0.1 g. 0.4 mmol). The flask was equipped with magnetic stirring and was lowered into an oil bath at 120° C.±5° C. for 30 minutes. The reaction mixture was cooled, dissolved in ether and washed with water. Drying and stripping the solvent gave 3.3 g (66%) of N-allyl N-(3-trifluoromethylphenyl)dichloroacetamide, the structure of which was confirmed by NMR. IR and MS.

EXAMPLE 3

This example illustrates the preparation of N-allyl N-(4-chlorophenyl)-(3-chloro)phenylchloroacetamide using a Pd(O) catalyst.

Following the procedures of Example 1. O-allyl N-(4-chlorophenyl)-(3-chloro)phenylchloroacetamidate (6.2 g) and Pd(PPh3)4 (0.3 g) were heated at 120–125° C. for 2 hours. The reaction mixture was cooled, diluted with ethyl ether and passed through an alumina pad to remove the metal catalyst. The ether was evaporated off to yield 4.5 g (72%) of N-allyl N-(4-chlorophenyl)-(3-chloro)phenylchloroacetamide, the structure of which was confirmed by NMR. IR and MS.

EXAMPLE 4

This example illustrates the preparation of N-allyl N-(3-trifluoromethylphenyl)dichloroacetamide using a Pd(O) catalyst.

Following the procedure of Example 1. O-allyl N-(3-trifluoromethylphenyl)dichloroacetamidate (3.6 g) and Pd(PPh3)4 (0 2 g) were heated at 120–130° C. for 1 hour to yield 2.0 g (56%) of N-allyl N-(3-trifluoromethylphenyl)dichloroacetamide, the structure of which was confirmed by NMR, IR and MS.

EXAMPLE 5

This example illustrates the preparation of M-(1-methyl)allyl N-(3-trifluoromethylphenyl)dichloroacetamide using a Pd(O) catalyst.

Following the procedure of Example 1, 0-crotyl N-(3-trifluoromethylphenyl)dichloroacetamidate (7.0 g) and Pd(PPh3)4 (0.2 g) were heated at 120–125° C. for 2 hours to yield 4.g g (70%) of N-(1-methyl)allyl N-(3-trifluoromethylphenyl)dichloroacetamide, the structure of which was confirmed by NMR. IR and MS.

EXAMPLE 6

This example illustrates the preparation of N-(1-methyl)allyl N-(3-trifluoromethylphenyl)dichloroacetamide using a Pd(II) catalyst.

Following the procedure of Example 2, O-crotyl N-(3-trifluoromethylphenyl)dichloroacetamidate (3.7 g) and Pd(OAc)2 (0.1 g) were heated at 120–130° C. for 30 min. to yield 2.g g (78%) of N-(1-methyl)allyl N-(3-trifluoromethylphenyl)dichloroacetamide, the structure of which was confirmed by NMR. IR and MS.

EXAMPLE 7

This example illustrates the preparation of N-crotyl N-(3-trifluoromethylphenyl)dichloroacetamide using a Pd(II) catalyst.

Following the procedure of Example 2. 0-(1-methyl)allyl N-(3-trifluoromethylphenyl)dichloroacetamidate (4.0 g) and Pd(OAc)2 (0.1 g) were heated at 120–130° C. for 1 hour to yield 3.0 g (75%) of N-crotyl N-(3-trifluoromethylphenyl)dichloroacetamide, the structure of which was confirmed by NMR, IR and MS.

EXAMPLE 8

This example illustrates the preparation of N-(1-phenyl)allyl N-(3-trifluoromethylphenyl)dichloroacetamide using a Pd(II) catalyst.

Following the procedure of Example 2, O-(3-phenyl)allyl N-(3-trifluoromethylphenyl)dichloroacetamidate (7.5 g) and Pd(OAc)2 (0.1 g) were heated at 120-130 3C for 3 hours to yield 6.1 g (81%) of N-(1-phenyl)allyl N-(3-trifluoromethylphenyl)dichloroacetamide, the structure of which was confirmed by NMR, IR and MS.

EXAMPLE 9

Following the procedure of Example 1. each of the following acetamidates is reacted with Pd(PPh3)4 at a temperature of about 120° C.±5–10° C. for from 30 min. to 2 hours to give the corresponding N-allyl amides:

O-allyl N-(3-trifluoromethylphenyl)-(3-fluoro)phenylchloroacetamidate

O-allyl N-(3-trifluoromethylphenyl)-(3-trifluoromethyl)phenylchloroacetamidate

O-allyl N-(3-trifluoromethylphenyl)-(3-chloro)phenylchloroacetamidate

O-allyl N-(3-trifluoromethylphenyl)-(3,N-difluoro)-phenylchloroacetamidate

O-allyl N-(3-cyanophenyl)-(3-chloro)phenylchloroacetamidate

O-allyl N-(3-chloro-4-fluorophenyl)-(3-chloro)phenylchloroacetamidate

Although the present invention has been described in some detail by way of example for purposes of clarity and understanding, it will be apparent that other arrangements and equivalents are possible and may be employed without departing from the spirit and scope of the invention. Therefore, the description and illustrations should not be construed as limiting the scope of the invention, which is delineated by the appended claims.

What is claimed is:

1. A process for the manufacture of a compound having the formula $$R-N-\overset{O}{\underset{\underset{R^1-C-C=C-R^4}{|}}{C}}-\overset{X}{\underset{|}{C}H}-Y \quad \quad I$$
$$\overset{|}{R^2} \quad \overset{|}{R^5}$$

wherein,

R is an unsubstituted or substituted aromatic group or an unsubstituted or substituted aliphatic group;

each of $R^1$, $R^2$, $R^3$, $R^4$ and $R^5$ is independently selected from hydrogen. $C_{1-4}$ alkyl or phenyl;

X is halogen; and

Y is halogen or an unsubstituted or substituted aromatic group;

which process comprises the rearrangement of a compound having the formula

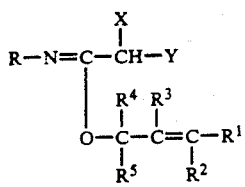

II wherein R, $R^1$, $R^2$, $R^3$, $R^4$, $R^5$, X and Y are defined above, by treatment of said compound II with a catalytic amount of a palladium(O) transition metal catalyst.

2. A process according to claim 1 wherein said palladium metal catalyst is selected from tetrakis(triphenylphosphine)palladium.

3. A process according to claim 1 wherein said process takes place at a temperature of from about 20° C. to about 160° C.

4. A process according to claim 1 wherein said process takes place at a temperature of from about 80° C. to about 150° C.

5. A process according to claim 2 wherein said process takes place at a temperature of from about 80° C. to about 150° C.

6. A process according to claim 1 wherein said palladium transition metal catalyst is present in an amount from about 0.01 to about 20.0 mole percent.

7. A process according to claim 1 wherein said palladium transition metal catalyst is present in an amount from about 0.1 to about 10.0 mole percent.

8. A process according to claim 2 wherein said palladium transition metal catalyst is present in an amount from about 0.1 to about 10.0 mole percent.

9. A process according to claim 1 wherein R is phenyl substituted at one to five of the ring carbon atoms with hydrogen, halogen, trifluoromethyl, cyano, $C_{1-4}$ alkyl or $C_{1-4}$ alkoxy.

10. A process according to claim 9 wherein $R^1$ is hydrogen, methyl or phenyl; each of $R^2$, $R^3$ and $R^5$ is hydrogen; and is hydrogen or methyl.

11. A process according to claim 10 wherein $R^1$ is methyl or phenyl and $R^4$ is hydrogen or methyl.

12. A process according to claim 10 wherein $R^1$ is hydrogen or methyl and $R^4$ is methyl.

13. A process according to claim 10 wherein X is chloro, and Y is chloro or phenyl substituted at one to five of the ring carbon atoms with hydrogen, halogen, trifluoromethyl, cyano, $C_{1-4}$ alkyl or $C_{1-4}$ alkoxy.

14. A process according to claim 13 wherein R is 3-trifluoromethylphenyl and Y is chloro. 3-chlorophenyl, 3-trifluoromethylphenyl. 3-fluorophenyl or 3,4-difluorophenyl.

* * * * *

UNITED STATES PATENT AND TRADEMARK OFFICE
CERTIFICATE OF CORRECTION

PATENT NO. : 5,011,990
DATED : April 30, 1991
INVENTOR(S) : Raymond A. Felix

It is certified that error appears in the above-indentified patent and that said Letters Patent is hereby corrected as shown below:

In Column 8, line 19, after the word "and" insert --$R^4$--.

Signed and Sealed this

Fifth Day of April, 1994

*Attest:*

BRUCE LEHMAN

*Attesting Officer*     *Commissioner of Patents and Trademarks*